(12) United States Patent
Lindquist et al.

(10) Patent No.: US 8,192,986 B2
(45) Date of Patent: Jun. 5, 2012

(54) COMPOSITIONS AND METHODS FOR TREATMENT OF PROTEIN MISFOLDING DISEASES

(75) Inventors: Susan L. Lindquist, Chestnut Hill, MA (US); Martin Duennwald, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 767 days.

(21) Appl. No.: 11/568,653

(22) PCT Filed: May 4, 2005

(86) PCT No.: PCT/US2005/015692
§ 371 (c)(1),
(2), (4) Date: Jul. 26, 2007

(87) PCT Pub. No.: WO2005/108599
PCT Pub. Date: Nov. 17, 2005

(65) Prior Publication Data
US 2008/0045607 A1    Feb. 21, 2008

Related U.S. Application Data

(60) Provisional application No. 60/568,726, filed on May 5, 2004.

(51) Int. Cl.
*C12Q 1/00* (2006.01)
*C12Q 1/02* (2006.01)
*G01N 33/53* (2006.01)

(52) U.S. Cl. ............... 435/375; 435/7.2; 435/4; 435/29

(58) Field of Classification Search .............. None
See application file for complete search history.

(56) References Cited

U.S. PATENT DOCUMENTS
2003/0073610 A1    4/2003 Lindquist et al.

OTHER PUBLICATIONS

Yoshida et al. XBP1 MRNA is induced by ATF6 and spliced by IRE1 in Response to ER Stress to Produce a Highly Active Transcription Factor; Cell, vol. 107 (2001) pp. 881-891.*
Sun et al. Endoplasmic Reticulum Stress as a Correlate of Cytotoxicity in Human Tumor Cells Exposed to Diinolylmethane In Vitro; Cell Stress and Chaperones, vol. 9, No. 1 (2004) pp. 76-87.*
Ryu et al. Endoplasmic Reticulum Stress and the Unfolded Protein Response in Cellular Models of Parkinson'S Disease; The Jornal of Neuroscience, vol. 22, No. 24 (2002) pp. 10690-10698.*
DePril et al., "Accumulation of Aberrant Ubiquitin Induces Aggregate Formation and Cell Death in Polyglutamine Diseases," Human Molecular Genetics, 13(16):1803-1813 (2004).
Kaufman, Randal J., "Orchestrating the unfolded protein response in health and disease," J. Clin. Invest. 110:1389-1398 (2002).
Kouroku, Y., et al., "Polyglutamine aggregates stimulate ER stress signals and caspase-12 activation," Hum Mol Genet Jun. 15; 11(13):1505-15 (2002).
Nishitoh, H., et al., "ASK1 is essential for endoplasmic reticulum stress-induced neuronal cell death triggered by expanded polyglutamine repeats," Genes Dev., Jun. 1; 16(11):1345-55 (2002).
Ron, D., "Translational control in the endoplasmic reticulum stress response," J. Clin. Invest. 110:1383-1388 (2002).
Yamanaka, K., et al., "Analysis of the two p97/VCP/Cdc48p proteins of Caenorhabditis elegans and their suppression of polyglutamine-induced protein aggregation," J. Strut Biol. Apr.-May; 146(12):242-50 (2004).

* cited by examiner

*Primary Examiner* — Rebecca Prouty
*Assistant Examiner* — Paul Martin
(74) *Attorney, Agent, or Firm* — Fish & Richardson P.C.

(57) ABSTRACT

Disclosed are methods for identifying compounds that modulate huntingtin mediated impairment of protein degradation pathways. Compounds identified by such screens can be used as candidate drugs for the treatment of prevention of polyglutamine diseases such as Huntington's Disease.

3 Claims, 6 Drawing Sheets

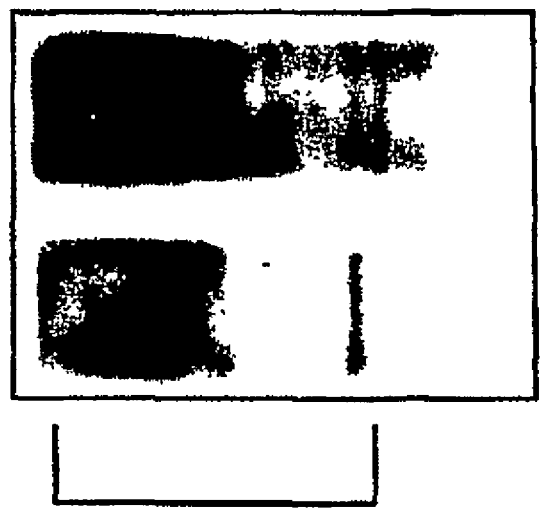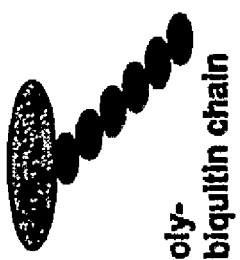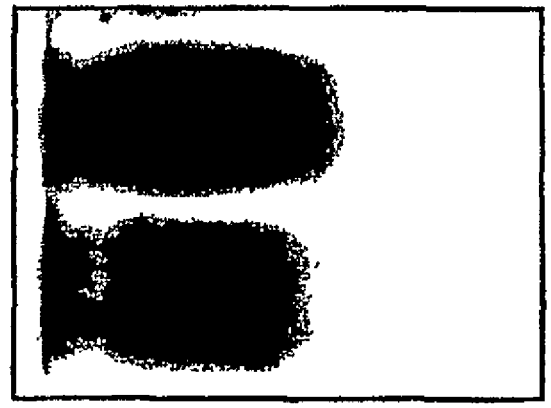
Fig. 1

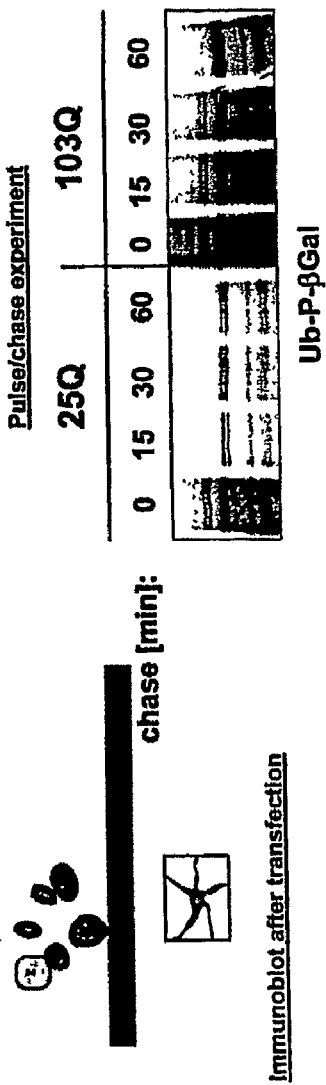
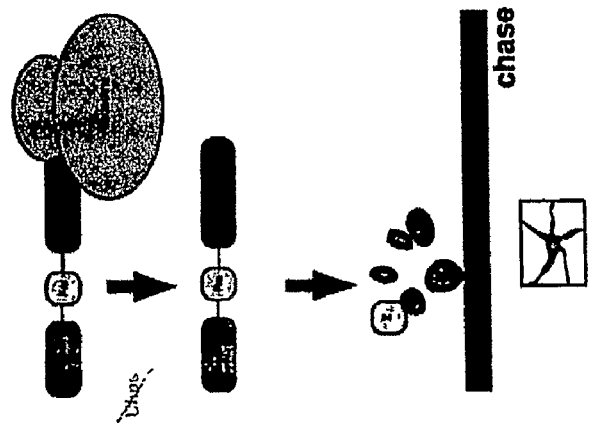
Fig. 3A  Fig. 3B  Fig. 3C  Fig. 3D

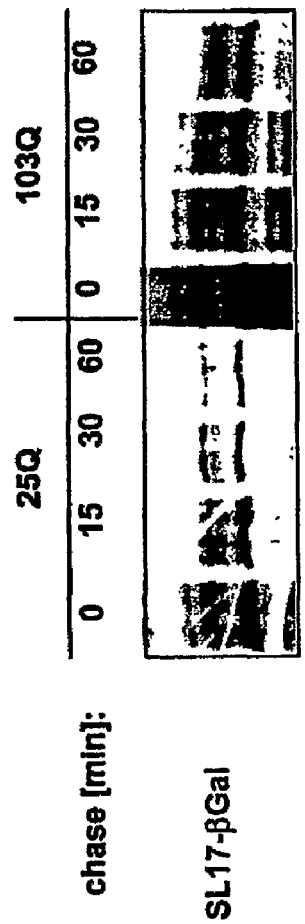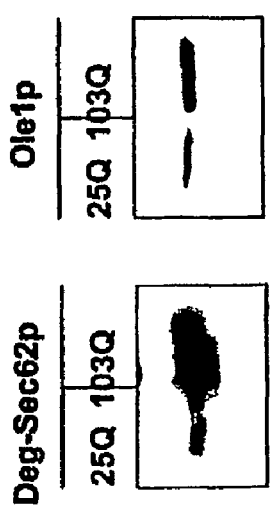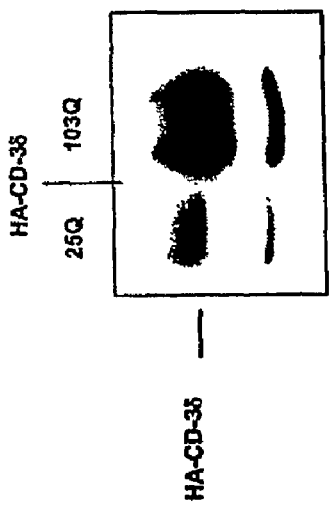

Fig. 6B  very low expression of huntingtin

Fig. 6D  high expression of huntingtin

IreC = constitutive active kinase inducing UPR
HACc = constitutive active transcription factor inducing UPR

COMPOSITIONS AND METHODS FOR TREATMENT OF PROTEIN MISFOLDING DISEASES

CROSS REFERENCE TO RELATED APPLICATIONS

This application is a national phase filing under 35 U.S.C. §371 of international application number PCT/US2005/015692, filed May 4, 2005, which claims priority from U.S. Provisional Application No. 60/568,726, filed May 5, 2004. The disclosures of the prior applications are considered part of (and are incorporated by reference in) the disclosure of this application.

STATEMENT AS TO FEDERALLY SPONSORED RESEARCH

This invention was made with Government support under grant number NS43664, NS44829, and GM25874, awarded by the National Institutes of Health. The Government may have certain rights in the invention.

FIELD OF THE INVENTION

This invention relates to methods for identifying compounds that modulate the function of abnormally processed proteins and compositions and methods for treatment of protein misfolding diseases.

BACKGROUND OF THE INVENTION

A class of diseases are caused by mutations involving the expansion of triplet sequence repeats. These disorders are called trinucleotide repeat diseases. Several trinucleotide repeat diseases have CAG as the repeated sequence. Since CAG codes for the amino acid glutamine, these CAG repeat disorders are known as polyglutamine diseases. Polyglutamine diseases include Spinobulbar muscular atrophy, Huntington disease, Dentatorubral-pallidoluysian atrophy, Spinocerebellar ataxia type 1, Spinocerebellar ataxia type 2, Spinocerebellar ataxia type 3, Spinocerebellar ataxia type 6, Spinocerebellar ataxia type 7, and Spinocerebellar ataxia type 17.

Huntington's Disease (HD) is a neurodegenerative disorder caused by an expansion of a CAG triplet repeat sequence in the huntingtin gene. This expansion results in the expression of the huntingtin protein with an extended polyglutamine region that misfolds and causes the demise of specific cells in the brains of HD patients.

Effective treatments are needed for Huntington's Disease as well as other polyglutamine diseases.

SUMMARY OF THE INVENTION

The invention is based, at least in part, on the discovery that huntingtin (Htt) specifically and severely inhibits the ubiquitin fusion degradation (UFD) and ER associated degradation (ERAD) protein degradation pathways in cells expressing a misfolded Htt protein. This Htt-mediated inhibition induces the unfolded protein response (UPR) and sensitizes the cells to endoplasmic reticulum (ER) stress. These results indicate an important role for the ER in Htt-mediated toxicity. The discoveries described herein permit the carrying out of screens to identify compounds that modulate Htt-mediated impairment of specific protein degradation pathways. Compounds identified by such screens can be used as candidate drugs for the treatment of prevention of polyglutamine diseases such as Huntington's Disease.

Described herein are methods of identifying a compound that prevents or suppresses huntingtin (Htt)-induced impairment of protein degradation, the method comprising: (1) providing a cell expressing a misfolded Htt protein and a ubiquitin fusion degradation (UFD) substrate; (2) contacting the cell with a candidate agent; (3) measuring the degradation of the UFD substrate in the cell; and (4) comparing the measured degradation of the UFD substrate in the presence of the candidate agent to degradation of the UFD substrate in the absence of the candidate agent, wherein if the degradation of the UFD substrate in the presence of the candidate agent is greater than degradation of the UFD substrate in the absence of the candidate agent, then the candidate agent is identified as a compound that prevents or suppresses Htt-induced impairment of protein degradation.

Also disclosed are methods of identifying a compound that prevents or suppresses Htt-induced impairment of protein degradation, the method comprising: (1) providing a cell expressing a misfolded Htt protein and an endoplasmic reticulum associated degradation (ERAD) substrate; (2) contacting the cell with a candidate agent; (3) measuring the degradation of the ERAD substrate in the cell; and (4) comparing the measured degradation of the ERAD substrate in the presence of the candidate agent to degradation of the ERAD substrate in the absence of the candidate agent, wherein if the degradation of the ERAD substrate in the presence of the candidate agent is greater than degradation of the ERAD substrate in the absence of the candidate agent, then the candidate agent is identified as a compound that prevents or suppresses Htt-induced impairment of protein degradation.

Also disclosed are methods of identifying a compound that prevents or suppresses Htt-induced impairment of protein degradation, the method comprising: (1) providing a cell expressing a misfolded Htt protein and an N-end rule substrate; (2) contacting the cell with a candidate agent; (3) measuring the degradation of the N-end rule substrate in the cell; and (4) comparing the measured degradation of the N-end rule substrate in the presence of the candidate agent to degradation of the N-end rule substrate in the absence of the candidate agent, wherein if the degradation of the N-end rule substrate in the presence of the candidate agent is greater than degradation of the N-end rule substrate in the absence of the candidate agent, then the candidate agent is identified as a compound that prevents or suppresses Htt-induced impairment of protein degradation.

Also disclosed are methods of identifying a compound that prevents or suppresses Htt-induced impairment of protein degradation, the method comprising: (1) contacting a cell expressing a misfolded Htt protein with a candidate agent; (2) measuring the amount of protein ubiquitination in the cell; and (3) comparing the measured amount of protein ubiquitination in the presence of the candidate agent to amount of protein ubiquitination in the absence of the candidate agent, wherein if the amount of protein ubiquitination in the presence of the candidate agent is less than the amount of protein ubiquitination in the absence of the candidate agent, then the candidate agent is identified as a compound that prevents or suppresses Htt-induced impairment of protein degradation.

Also disclosed are methods of identifying a compound that prevents or suppresses Htt-induced impairment of protein degradation, the method comprising: (1) contacting a cell expressing a misfolded Htt protein with a candidate agent; (2) measuring Htt-mediated induction of the unfolded protein response (UPR) in the cell; and (3) comparing the measured Htt-mediated induction of the UPR in the presence of the candidate agent to Htt-mediated induction of the UPR in the absence of the candidate agent, wherein if the Htt-mediated induction of the UPR in the presence of the candidate agent is less than Htt-mediated induction of the UPR in the absence of the candidate agent, then the candidate agent is identified as a compound that prevents or suppresses Htt-induced impairment of protein degradation. The UPR can be measured by detecting expression of a reporter construct controlled by the UPR-promoter element (UPRE).

Also disclosed are methods of identifying a compound that prevents or suppresses Htt-induced impairment of protein degradation, the method comprising: (1) contacting a cell with a candidate agent; (2) measuring induction of the UPR in the cell; and (3) measuring the level of misfolded proteins in the ER in the cell, wherein if the UPR is induced in the cell in the absence of an increase in the level of misfolded proteins in the ER of the cell, then the candidate agent is identified as a compound that prevents or suppresses Htt-induced impairment of protein degradation. The methods can also include evaluating the effectiveness of the candidate agent at suppressing or reducing Htt-mediated toxicity in a cell (e.g., a yeast cell).

Also disclosed are methods of identifying a compound that prevents or suppresses Htt-induced toxicity, the method comprising: (1) identifying a candidate agent that that activates the UPR; (2) contacting a cell expressing a misfolded Htt protein with the candidate agent; (3) culturing the cell in the presence of the candidate agent and under conditions that allow for expression of the misfolded Htt protein at a level that, in the absence of the candidate agent, is sufficient to induce toxicity in the cell; and (4) determining whether toxicity in the cell is less in the presence of the candidate agent as compared to in the absence of the candidate agent, wherein if the toxicity is less in the presence of the candidate agent than in the absence of the candidate agent, then the candidate agent is identified as a compound that prevents or suppresses Htt-induced toxicity.

Also disclosed are methods of identifying a compound that prevents or suppresses Htt-induced impairment of protein degradation, the method comprising: (1) contacting a cell expressing a misfolded Htt protein with a candidate agent; (2) measuring the interaction of the misfolded Htt protein with a protein complex comprising p97, Ufd1, and Np14; and (3) comparing the measured interaction of the misfolded Htt protein with the protein complex in the presence of the candidate agent to the interaction of the misfolded Htt protein with the protein complex in the absence of the candidate agent, wherein if the interaction of the misfolded Htt protein with the protein complex in the presence of the candidate agent is less than the interaction of the misfolded Htt protein with the protein complex in the absence of the candidate agent, then the candidate agent is identified as a compound that prevents or suppresses Htt-induced impairment of protein degradation. The method can also include determining whether the candidate agent binds to the misfolded Htt protein.

In addition to a misfolded Htt protein, as described above, any misfolded polyglutamine protein can be used in the methods described herein. The following is a list of exemplary polyglutamine diseases (as well as specific disease associated proteins and the approximate length of the polyglutamine repeat that is associated with disease): Spinobulbar muscular atrophy (androgen receptor; disease repeat length of 38-62); Huntington disease (huntingtin; disease repeat length of 36-121); Dentatorubral-pallidoluysian atrophy (atrophin-1; disease repeat length of 49-88); Spinocerebellar ataxia type 1 (ataxin-1; disease repeat length of 39-82); Spinocerebellar ataxia type 2 (ataxin-2; disease repeat length of 36-63); Spinocerebellar ataxia type 3 (ataxin-3; disease repeat length of 55-84); Spinocerebellar ataxia type 6 ($\alpha 1_A$-voltage-dependent calcium channel subunit; disease repeat length of 21-33); Spinocerebellar ataxia type 7 (ataxin-7; disease repeat length of 37-306); and Spinocerebellar ataxia type 17 (TATA binding protein; disease repeat length of 45-63).

The misfolded Htt protein used in any of the methods described herein can be a toxicity inducing form of Htt. For example, the misfolded Htt protein can comprise a polyglutamine repeat of at least 103 amino acids and induce toxicity in a cell expressing the protein.

The cell used in any of the methods described herein can be, for example, a yeast cell or a mammalian cell (e.g., a neuronal cell such as a cell derived from the PC12 cell line).

Also disclosed are methods of treating an individual suffering from a polyglutamine disease (e.g., Huntington's Disease), the method comprising inducing, in neuronal cells of the individual, the expression or activity of a protein that induces UPR.

Also disclosed are methods of suppressing or reducing polyglutamine (e.g., Htt)-mediated toxicity in a cell, the method comprising inducing the expression or activity of a protein that induces UPR.

The protein that induces UPR, whose expression or activity is induced in the above methods, can be, for example, IRE1α, IRE1β, ATF6, PERK, and/or XBP-1.

In some embodiments, the protein that induces UPR is IRE1α or IRE1β and the method comprises stimulating the activity of IRE1α or IRE1β by increasing one or more of dimer formation, phosphorylation, kinase activity, or RNase activity of the protein.

In some embodiments, the protein that induces UPR is ATF6 and the method comprises stimulating the activity of ATF6 by increasing proteolytic processing of the protein.

In some embodiments, the protein that induces UPR is XBP-1 and the method comprises stimulating the activity of XBP-1 by increasing splicing of the protein.

In some embodiments, the method comprises inhibiting the interaction of BIP with one or more of IRE1α, IRE1β, ATF6, or PERK.

Also disclosed are methods of treating an individual suffering from a polyglutamine disease (e.g., Huntington's Disease), the method comprising inducing the UPR in neuronal cells of the individual.

Also disclosed are methods of suppressing or reducing polyglutamine (e.g., Htt)-mediated toxicity in a cell, the method comprising inducing the UPR in the cell.

In some embodiments, the above methods comprise inducing UPR in the cell without inducing protein misfolding in the ER.

Also disclosed are methods of treating an individual suffering from polyglutamine disease (e.g., Huntington's Disease), the method comprising inhibiting ER stress in neuronal cells of the individual.

Also disclosed are methods of suppressing or reducing polyglutamine (e.g., Htt)-mediated toxicity in a cell, the method comprising inhibiting ER stress in the cell.

Also disclosed are methods of treating an individual suffering from polyglutamine disease (e.g., Huntington's Disease), the method comprising administering to the individual a pharmaceutical composition comprising a therapeutically effective amount of a compound identified by any of the methods described herein.

The treatment methods described herein comprise administering a therapeutically effective amount of a compound (e.g., drug) to a subject. The compound can be a small molecule compound, a peptidomimetic, a nucleic acid (e.g., an antisense molecule), or a polypeptide. The compound can be a natural product, synthetic compound, or semi-synthetic compound. Optionally, the compound for treatment is formulated with a pharmaceutically acceptable carrier. The compound can be administered alone or in combination with another method or methods of treating such an individual (e.g., in combination with another drug, surgery or stem cell or neuronal cell implantation).

A compound identified by a screen described herein can be tested for effectiveness in vivo (e.g., in a mammal such as a mouse or a human). An exemplary in vivo model is a transgenic mouse whose genome comprises a transgene that encodes a polyglutamine protein (e.g., Htt) and is expressed in the mouse (e.g., in neuronal cells) in such a manner that it results in cell toxicity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1 depicts the stabilization of ubiquitinated proteins by misfolded huntingtin.

FIGS. 2A-2D depict the stabilization of N-end rule substrates by huntingtin.

FIGS. 3A-3D depict the inhibition of the ubiquitin fusion degradation pathway by huntingtin.

FIGS. 4A-4C depict the inhibition of degradation of endoplasmic reticulum associated degradation substrates by huntingtin.

FIGS. 6A-6E depict enhanced huntingtin toxicity by a dysfunctional unfolded protein response and ameliorated huntingtin toxicity by an activated unfolded protein response.

DETAILED DESCRIPTION OF THE INVENTION

Figure 5B:
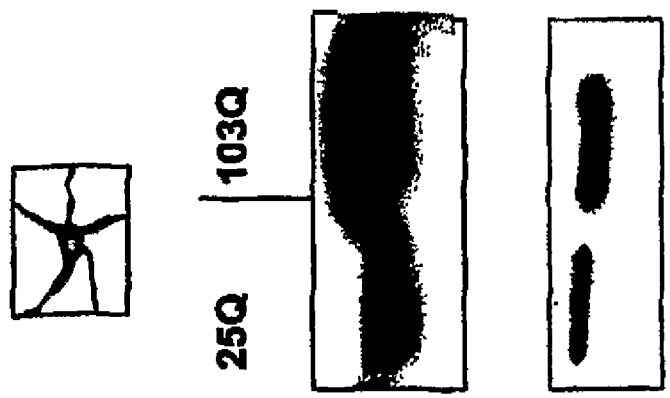
FIGS. 5A-5B depict the induction of the unfolded protein response by misfolded huntingtin.

Huntington's Disease is caused by an expansion of a CAG triplet repeat sequence in the huntingtin gene, which results in the expression of a huntingtin protein with an extended polyglutamine region that misfolds and causes the demise of specific cells in the brains of Huntington's Disease patients.

The experimental results described herein demonstrate that that protein turn-over by the ubiquitin-proteasome system (UPS) is impaired in yeast cells expressing misfolded huntingtin. Surprisingly, the turnover of endoplasmic reticulum associated degradation (ERAD) substrates was found to be more dramatically affected than that of other proteins. The impairment of ERAD causes stress in the ER resulting in the activation of the unfolded protein response (UPR) and a higher sensitivity to conditions that cause protein misfolding in the ER. Moreover, blocking the UPR resulted in a pronounced increase in toxicity of misfolded huntingtin. Experiments in neuronal cells confirmed the impairment of ERAD and induction of the UPR by misfolded huntingtin in a higher eukaryotic system.

An ER-specific apoptotic pathway, marked by caspase-12 activation, was found to be induced in cells expressing misfolded huntingtin. Not only were general components of the UPS like the 26S proteasome and ubiquitin shown to co-localize with misfolded huntingtin, but more specifically a protein complex essential for ERAD consisting of p97, Ufd1, and Npl4 was also sequestered into huntingtin aggregates. The mislocalization of the p97/Ufd1/Npl4 complex to huntingtin aggregates suggests the mechanism responsible for the impairment of ERAD resulting from the presence of misfolded huntingtin. These experimental results point to a major role of the ER in huntingtin-mediated toxicity and also serve as a paradigm for the cross-talk between different cellular compartments in response to protein misfolding.

Polyglutamine Diseases

A class of diseases are caused by mutations involving the expansion of triplet sequence repeats. These disorders are called trinucleotide repeat diseases. Several trinucleotide repeat diseases have CAG as the repeated sequence. Since CAG codes for the amino acid glutamine, these CAG repeat disorders are known as polyglutamine diseases.

Although the genes involved in the different polyglutamine diseases have little in common, the disorders nonetheless follow a similar course. Each polyglutamine disease is characterized by a progressive degeneration of a distinct group of nerve cells. Above a certain threshold, the greater the number of glutamine repeats in a protein, the earlier the onset of disease and the more severe the symptoms. Certain symptoms of the different diseases are similar, and usually affect people in midlife. Given the similarities in symptoms, the polyglutamine diseases are thought to progress via common cellular mechanisms. Accordingly, the experimental findings described herein implicating ER stress as a major cause for Htt-mediated toxicity is also expected to apply to other polyglutamine proteins causing other polyglutamine diseases.

The following is a list of exemplary polyglutamine diseases (as well as the specific proteins having the polyglutamine repeat and the approximate length of the repeat that is associated with disease): Spinobulbar muscular atrophy (androgen receptor; disease repeat length of 38-62); Huntington disease (huntingtin; disease repeat length of 36-121); Dentatorubral-pallidoluysian atrophy (atrophin-1; disease repeat length of 49-88); Spinocerebellar ataxia type 1 (ataxin-1; disease repeat length of 39-82); Spinocerebellar ataxia type 2 (ataxin-2; disease repeat length of 36-63); Spinocerebellar ataxia type 3 (ataxin-3; disease repeat length of 55-84); Spinocerebellar ataxia type 6 ($\alpha 1_A$-voltage-dependent calcium channel subunit; disease repeat length of 21-33); Spinocerebellar ataxia type 7 (ataxin-7; disease repeat length of 37-306); and Spinocerebellar ataxia type 17 (TATA binding protein; disease repeat length of 45-63).

Yeast Cells

Yeast (e.g., *Saccharomyces cerevisiae*) is an extraordinarily powerful system for studying complex biological problems. There are numerous advantaged to using yeast as a model system. These include: 1) switching readily between haploid and diploid genetics; 2) the ease of site directed mutagenesis; 3) the availability of many expression vectors; 4) methods for genetic and chemical screens that can be performed at a fraction of the price in time and materials required in other systems; 5) a chaperone machinery, particularly relevant for problems involving protein folding, that is extensively characterized; and 6) special strains with greatly enhanced drug sensitivities. Finally, because the yeast genome was the first eukaryotic genome to be sequenced it is currently the single best-characterized eukaryotic cell. Yeast can be used as a model system or living test tubes for studying protein misfolding (see, e.g., Outeiro et al. (2003) Science 302:1772).

Described herein are experimental results demonstrating that yeast cells expressing a misfolded Htt protein have specific impairments in their protein degradation machinery and can therefore be used to investigate Huntington's Disease as well as other polyglutamine diseases characterized by a polyglutamine expansion.

Yeast strains that can be used in the compositions and methods described herein include, but are not limited to, *Saccharomyces cerevisiae, Saccharomyces uvae, Saccharomyces kluyveri, Schizosaccharomyces pombe, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans*. Although much of the discussion herein relates to *Saccharomyces cerevisiae* which expresses a polyglutamine protein (e.g., Htt), this is merely for illustrative purposes. Other yeast strains can be substituted for *S. cerevisiae*.

Certain aspects of the disclosure relate to screening methods for identifying candidate therapeutic agents (e.g., pharmaceutical, chemical, or genetic agents). The methods described herein can be carried out in yeast strains bearing mutations in the ERG6 gene, the PDR1 gene, the PDR3 gene, the PDR5 gene, and/or any other gene which affects membrane efflux pumps and/or increases permeability for drugs.

Polyglutamine Tract Containing Proteins

In certain aspects, compositions and methods disclosed herein use a protein (e.g., Htt) causally associated with the occurrence of a polyglutamine disease. The protein contains an extended polyglutamine tract (e.g., at least 30, 40, 50, 60, 70, 80, 90, 100, 110, 120, 130 140, 150, or more consecutive glutamines) that causes misfolding of the protein. In some embodiments, the polyglutamine tract renders the protein toxic to cells (e.g., yeast cells or neuronal cells) that express the protein.

Cells (e.g., yeast cells) expressing a toxicity-inducing form and/or amount of a protein (e.g., Htt) comprising an extended polyglutamine tract (or a biologically active fragment thereof) can be screened to identify compounds that rescue growth and inhibit toxicity mediated by the protein. In some embodiments, cells expressing the polyglutamine tract-containing protein can be screened to identify compounds that prevent or suppress impairment of protein degradation in the cell caused by the protein.

An exemplary Htt-expressing yeast strain that can be used in the methods described herein (including use in a growth rescue screen) is yeast expressing a fusion protein comprising a FLAG tag and an expanded Htt polyQ (103) domain, as described in Meriin et al. (2002) J. Cell Biol. 158:591. A protein containing Htt polyQ (103) can also be used for screens in mammalian cells.

In certain embodiments, fusion proteins including at least the portion of the extended polyglutamine tract that causes misfolding and/or toxicity of the disease protein may be used. For example, a portion of the protein may be fused with a second domain. The second domain of the fusion proteins can be selected from the group consisting of: an immunoglobulin element, a dimerizing domain, a targeting domain, a stabilizing domain, and a purification domain. Alternatively, a portion of the polyglutamine protein can be fused with a heterologous molecule such as a detection protein. Exemplary detection proteins include: (1) a fluorescent protein such as green fluorescent protein (GFP), cyan fluorescent protein (CFP) or yellow fluorescent protein (YFP); (2) an enzyme such as β-galactosidase or alkaline phosphatase (AP); and (3) an epitope such as glutathione-S-transferase (GST) or hemagluttin (HA). To illustrate, an Htt protein can be fused to GFP at the N- or C-terminus or other parts of the Htt protein. These fusion proteins provide methods for rapid and easy detection and identification of the Htt protein in the recombinant host cell, exemplified herein by the yeast cell.

Nucleic Acid Vectors for Expression in Yeast

A nucleic acid encoding a component of an assay system described herein (e.g., a polyglutamine protein such as Htt, an N-end rule substrate, a UFD substrate, an ERAD substrate, a UPR reporter construct, and/or an inducer of UPR) may be transfected into a yeast cell using nucleic acid vectors that include, but are not limited to, plasmids, linear nucleic acid molecules, artificial chromosomes, and episomal vectors.

Three well known systems used for recombinant plasmid expression and replication in yeast cells include integrative plasmids, low-copy-number ARS-CEN plasmids, and high-copy-number 2μ plasmids. See Sikorski, "Extrachromsomoal cloning vectors of *Saccharomyces cerevisiae*," in Plasmid, A Practical Approach, Ed. K. G. Hardy, IRL Press, 1993; and Yeast Cloning Vectors and Genes, Current Protocols in Molecular Biology, Section II, Unit 13.4, Eds., Ausubel et al., 1994.

An example of the integrative plasmids is YIp, which is maintained at one copy per haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells.

An example of the low-copy-number ARS-CEN plasmids is YCp, which contains the autonomous replicating sequence (ARS1) and a centromeric sequence (CEN4). These plasmids are usually present at 1-2 copies per cell. Removal of the CEN sequence yields a YRp plasmid, which is typically present in 100-200 copies per cell. However, this plasmid is both mitotically and meiotically unstable.

An example of the high-copy-number 2μ plasmids is YEp, which contains a sequence approximately 1 kb in length (named the 2μ sequence). The 2μ sequence acts as a yeast replicon giving rise to higher plasmid copy number. However, these plasmids are unstable and require selection for maintenance. Copy number is increased by having on the plasmid a selection gene operatively linked to a crippled promoter.

A wide variety of plasmids can be used in the compositions and methods described herein. In one embodiment, the plasmid is an integrative plasmid (e.g., pRS303, pRS304, pRS305 or pRS306 or other integrative plasmids). In further embodiments, the plasmid is an episomal plasmid (e.g., p426GPD, p416GPD, p426TEF, p423GPD, p425GPD, p424GPD or p426GAL).

Regardless of the type of plasmid used, yeast cells are typically transformed by chemical methods (e.g., as described by Rose et al., 1990, Methods in Yeast Genetics, Cold Spring Harbor Laboratory Press, Cold Spring Harbor, N.Y.). The cells are typically treated with lithium acetate to achieve transformation efficiencies of approximately $10^4$ colony-forming units (transformed cells)/μg of DNA. Yeast perform homologous recombination such that the cut, selectable marker recombines with the mutated (usually a point mutation or a small deletion) host gene to restore function. Transformed cells are then isolated on selective media.

The yeast vectors (plasmids) described herein typically comprise a yeast origin of replication, an antibiotic resistance gene, a bacterial origin of replication (for propagation in bacterial cells), multiple cloning sites, and a yeast nutritional gene for maintenance in yeast cells. The nutritional gene (or "auxotrophic marker") is most often one of the following: 1) TRP1 (Phosphoribosylanthranilate isomerase); 2) URA3 (Orotidine-5'-phosphate decarboxylase); 3) LEU2 (3-Isopropylmalate dehydrogenase); 4) HIS3 (Imidazoleglycerolphosphate dehydratase or IGP dehydratase); or 5) LYS2 (α-aminoadipate-semialdehyde dehydrogenase).

The yeast vectors (plasmids) described herein may also comprise promoter sequences. A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively linked" and "operatively positioned" mean that a promoter is in a correct functional location and/or orientation in relation to a nucleic acid sequence to control transcriptional initiation and/or expression of that sequence.

A promoter may be one naturally associated with a nucleic acid sequence, as may be obtained by isolating the 5' non-coding sequences located upstream of the coding segment and/or exon. Such a promoter can be referred to as "endogenous." Alternatively, a promoter may be a recombinant or heterologous promoter, which refers to a promoter that is not normally associated with a nucleic acid sequence in its natural environment. Such promoters may include promoters of other genes and promoters not "naturally occurring." The promoters employed may be either constitutive or inducible.

For example, various yeast-specific promoters (elements) may be employed to regulate the expression of a RNA in yeast cells. Examples of inducible yeast promoters include GAL1-10, GAL1, GALL, GALS, TET, VP16 and VP16-ER. Examples of repressible yeast promoters include Met25. Examples of constitutive yeast promoters include glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), and MRP7. Autonomously replicating expression vectors of yeast containing promoters inducible by glucocorticoid hormones have also been described (Picard et al., 1990), including the glucorticoid responsive element (GRE). These and other examples are described in Mumber et al., 1995; Ronicke et al., 1997; Gao, 2000, all incorporated herein by reference. Yet other yeast vectors containing constitutive or inducible promoters such as alpha factor, alcohol oxidase, and PGH may be used. For reviews, see Ausubel et al. and Grant et al., 1987.

To express a polyglutamine protein such as Htt in yeast cells, a variety of expression constructs that permit different levels of expression and different patterns can be used. Constitutive promoters allow expression in normal media, but inducible promoters allow to control the levels and timing of expression. Controllable expression is of particular interest when dealing with toxic proteins (e.g., to turn on expression of the toxic protein at a particular time point).

Screening Assays

Certain aspects of the present disclosure provide methods (assays) of screening for a candidate drug (agent or compound) and identifying a drug for treating a polyglutamine disease. A "candidate drug" as used herein, is any substance with a potential to reduce, interfere with or block activities/functions of a polyglutamine protein (e.g., Htt). Various types of candidate drugs may be screened by the methods described herein, including nucleic acids, polypeptides, small molecule compounds, and peptidomimetics. In some cases, genetic agents can be screened by contacting the yeast cell with a nucleic acid construct encoding for a gene. For example, one may screen cDNA libraries expressing a variety of genes, to identify therapeutic genes for the diseases described herein. In other examples, one may contact the yeast cell with other proteins or polypeptides which may confer the therapeutic effect.

In certain embodiments, candidate drugs can be screened from large libraries of synthetic or natural compounds. One example is an FDA approved library of compounds that can be used by humans. In addition, synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.), and a rare chemical library is available from Aldrich (Milwaukee, Wis.). Combinatorial libraries are available and can be prepared. Alternatively, libraries of natural compounds in the form of bacterial, fungal, plant and animal extracts are also available, for example, Pan Laboratories (Bothell, Wash.) or MycoSearch (NC), or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can immediately be used in the screens.

Potential drugs may include a small molecule. Examples of small molecules include, but are not limited to, small peptides or peptide-like molecules (e.g., a peptidomimetic). As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics.

In certain embodiments, such candidate drugs also encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl, sulphydryl or carboxyl group.

Other suitable candidate drugs may include antisense molecules, ribozymes, and antibodies (including single chain antibodies), each of which would be specific for the target molecule. For example, an antisense molecule that binds to a translational or transcriptional start site, or splice junctions, would be ideal candidate inhibitors.

One embodiment contemplates screening assays using fluorescent resonance energy transfer (FRET). FRET occurs when a donor fluorophore is in close proximity (10-60 A) to an acceptor fluorophore, and when the emission wavelength of the first overlaps the excitation wavelength of the second (Kenworthy A K et al., 2001. Methods. 24:289-96). FRET should occur when cyan fluorescent protein (CFP) and yellow fluorescent protein (YFP) fusion proteins are actually part of the same complex.

For example, an Htt protein is fused to CFP (under the regulation of a GAL1-10 promoter) and a component of the p97/Ufd1/Np14 complex is fused to YFP. Cells are grown in galactose to induce expression of the Htt protein. Upon induction, cells produce the fusion proteins, which aggregate and bring the CFP and YFP close together. Because proteins in the aggregates are tightly packed, the distance between the CFP and YFP is less than the critical value of 100 A that is necessary for FRET to occur. In this case, the energy released by the emission of CFP will excite the YFP, which in turn will emit at its characteristic wavelength. FRET based screening can be used to identify candidate compounds including, drugs, genes or other factors that can disrupt the interaction of CFP and YFP by maintaining the proteins in a state that does not allow aggregation to occur.

One embodiment contemplates screening assays using fluorescence activated cell sorting (FACS) analysis. FACS is a technique well known in the art, and provides the means of scanning individual cells for the presence of fluorescently labeled/tagged moiety. The method is unique in its ability to provide a rapid, reliable, quantitative, and multiparameter analysis on either living or fixed cells. For example, the misfolded Htt protein can be suitably labeled, and provide a useful tool for the analysis and quantitation of protein aggregation as a result of other genetic or growth conditions of individual yeast cells as described above.

In particular embodiments, methods of the present disclosure relate to determining polyglutamine protein (e.g., Htt) associated toxicity. One of the strongest aspects of yeast is the possibility of performing high throughput screens that may identify genes, peptides and other compounds with the potential to ameliorate toxicity. For example, the BIOSCREEN C™ (Labsystem) permits the growth of up to 200 cell cultures at the same time, under different conditions. Growth rates are monitored optically, recorded automatically, and stored as digital files for further manipulations. Growth will be monitored in the presence of genetic libraries, chemicals, drugs, etc. to identify those that give a selective growth advantage. Mutants and chemicals from a variety of sources will be tested.

In particular embodiments, methods of the present disclosure relate to determining proteasomal impairment caused by a polyglutamine protein (e.g., Htt). This can be done, for example, be means of an assay that utilizes fusions between ubiquitin and β-galactosidase molecules with different N termini (see, e.g., Bachmair A, et al., 1986. Science. 234:179-86). Such assay allows qualitative assessment of proteasome activity in yeast.

Certain embodiments provide methods of further testing those potential drugs that have been identified in the yeast system, in other model systems. The model systems include, but are not limited to, worms, flies, mammalian cells, and in vivo animal models (e.g., a mouse transgenic for a polyglutamine protein such as Htt).

Methods of Treatment

Certain aspects of the present disclosure relate to methods of treating a subject suffering from a polyglutamine disease. As described above, polyglutamine diseases include, but are not limited to: Spinobulbar muscular atrophy; Huntington disease; Dentatorubral-pallidoluysian atrophy; Spinocerebellar ataxia type 1; Spinocerebellar ataxia type 2; Spinocerebellar ataxia type 3; Spinocerebellar ataxia type 6; Spinocerebellar ataxia type 7; and Spinocerebellar ataxia type 17.

Certain embodiments contemplate initial testing and treatment of animal-models with candidate drugs identified by screens described herein. Suitable animal-model for the polyglutamine diseases will be selected, and treatment will involve the administration of the drugs, in an appropriate pharmaceutical formulation, to the animal. Administration will be by any route that could be utilized for clinical or non-clinical purposes, including but not limited to oral, nasal, buccal, or topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site. Determining the effectiveness of a compound in vivo may involve a variety of different criteria.

In certain embodiments, the present disclosure provides methods of treating a subject (patient or individual) suffering from a polyglutamine disease. In other embodiments, the disclosure provides methods of preventing or reducing the onset of such diseases in a subject. For example, an individual who is at risk of developing Huntington Disease (e.g., an individual whose family history includes Huntington Disease) and/or has signs he/she will develop Huntington Disease can be treated by the present methods. These methods comprise administering to the individual an effective amount of a compound that are identified by the screening methods as described above. These methods are particularly aimed at therapeutic and prophylactic treatments of animals, and more particularly, humans.

Formulation and Administration

In certain embodiments, candidate drugs (compounds) may be formulated in combination with a suitable pharmaceutical carrier. Such formulations comprise a therapeutically effective amount of the drug, and a pharmaceutically acceptable carrier (excipient). Examples of suitable carriers are well known in the art. To illustrate, the pharmaceutically acceptable carrier can be an aqueous solution or physiologically acceptable buffer. Optionally, the aqueous solution is an acid buffered solution. Such acid buffered solution may comprise hydrochloric, sulfuric, tartaric, phosphoric, ascorbic, citric, fumaric, maleic, or acetic acid. Alternatively, such carriers include, but are not limited to, saline, buffered saline, dextrose, water, glycerol, ethanol, and combinations thereof. Formulations will suit the mode of administration, and are well within the skill of the art.

In certain embodiments of such methods, one or more drugs can be administered, together (simultaneously) or at different times (sequentially). In addition, such drugs can be administered with another type(s) of drug(s) for treating a polyglutamine disease.

The phrase "therapeutically effective amount," as used herein, refers to an amount that is sufficient or effective to prevent or treat (prevent the progression of or reverse) a polyglutamine disease, including alleviating symptoms of such diseases.

The dosage range depends on the choice of the drug, the route of administration, the nature of the formulation, the nature of the subject's condition, and the judgment of the attending practitioner. Wide variations in the needed dosage, however, are to be expected in view of the variety of drugs available and the differing efficiencies of various routes of administration. For example, oral administration would be expected to require higher dosages than administration by intravenous injection. Variations in these dosage levels can be adjusted using standard empirical routines for optimization, as is well understood in the art.

The following are examples of the practice of the invention. They are not to be construed as limiting the scope of the invention in any way.

EXAMPLES

Example 1

Misfolded Huntingtin Stabilizes Ubiquitinated Proteins

Protein extracts of yeast cells and PC12 cells (rat neuronal cells) expressing huntingtin with 25 Qs and 103Qs, respectively, were subjected to immunoblotting using an anti-ubiquitin antibody. In both systems, cells expressing 103Q huntingtin showed increased levels of ubiquitinated proteins (FIG. 1). These results indicated that expression of a misfolded huntingtin protein resulted in a decrease in the turnover of ubiquitinated proteins in yeast cells as well as in neuronal cells.

Example 2

Huntingtin Stabilizes N-End Rule Substrates

The N-end-rule pathway is depicted in FIG. 2A. N-end-rule substrates were co-expressed in yeast (FIGS. 2B and 2C) or PC 12 cells (FIG. 2D) with 25 or 103 Q huntingtin. The impairment of lacZ or GFP reporter degradation in the presence of 103 Q huntingtin was monitored by an overlay assay (FIG. 2B), pulse chase analysis (FIG. 2C), or immunoblotting (FIG. 2D). These results indicated that expression of a misfolded huntingtin protein resulted in the stabilization of N-end rule substrates in yeast cells as well as in neuronal cells.

Example 3

Huntingtin Specifically Inhibits the Ubiquitin Fusion Degradation (UFD Pathway UFD substrates were co-expressed in yeast (FIGS. 3B and 3C) or PC 12 cells (FIG. 3D) with 25 and 103 Q huntingtin. The impairment of lacZ or GFP reporter degradation in the presence of 103 Q huntingtin was monitored by a quantitative B-Gal-assay (FIG. 3B), pulse chase analysis (FIG. 3C), or immunoblotting (FIG. 3D). These results indicated that expression of a misfolded huntingtin protein severely inhibited turnover in the UFD pathway in yeast cells and neuronal cells.

Example 4

Misfolded Huntingtin Inhibits the Degradation of Endoplasmic Reticulum Associated Degradation (ERAD) Substrates ERAD (turn-over of membrane proteins and lumenal proteins) substrates were co-expressed in yeast (FIGS. 4A and 4B) or PC 12 cells (FIG. 4C) with 25 and 103 Q huntingtin. The impairment of degradation of the reporter proteins in the presence of 103 Q huntingtin was monitored by immunoblotting (FIGS. 4A and 4C) or pulse chase analysis (FIG. 4B). These results indicated that expression of a misfolded huntingtin protein severely inhibited turnover of ERAD substrates in yeast cells and neuronal cells.

Example 5

Misfolded Huntingtin Induces the Unfolded Protein Response (UPR)

Figure 5A:
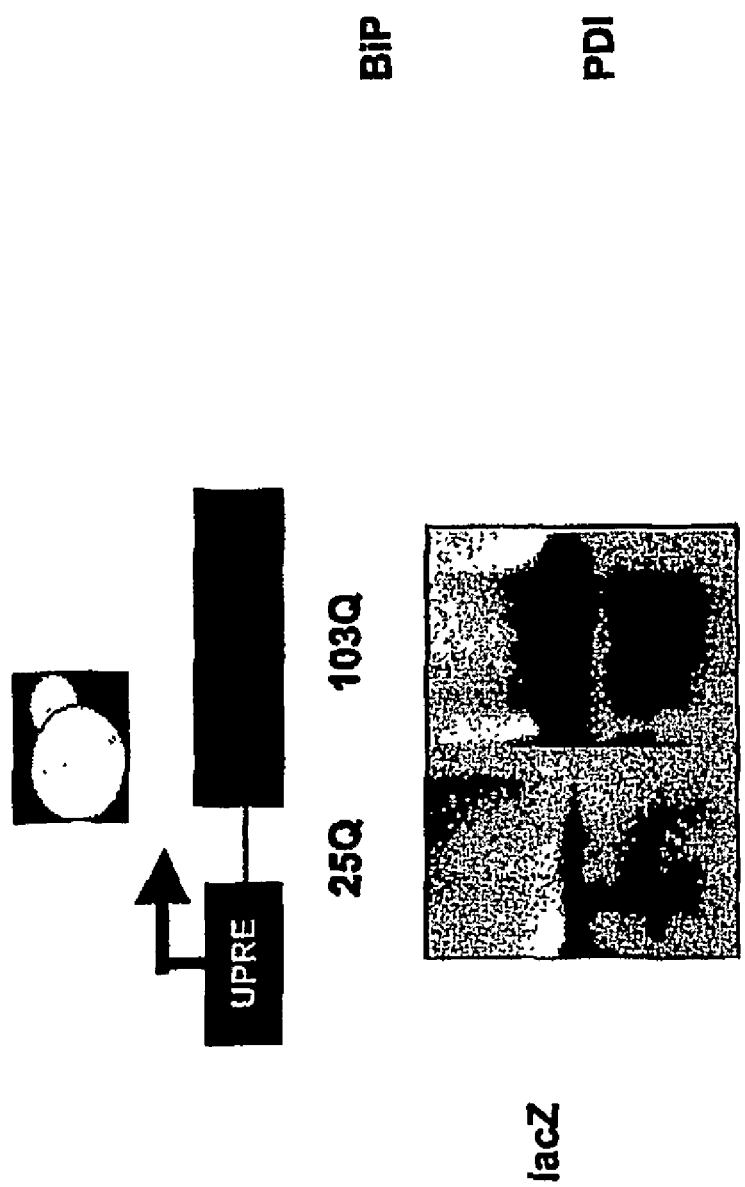

The induction of the UPR in yeast expressing 103Q huntingtin (FIG. 5A) was demonstrated by employing a reporter construct controlled by the UPR-promoter element (UPRE) (FIG. 5A). UPR induction of PC12 cells expressing 103Q huntingtin was reflected by higher levels of the UPR clients BiP and PDI (FIG. 5B). These results indicated that expression of a misfolded huntingtin protein induced the UPR in neuronal cells.

Example 6

Figure 6C:
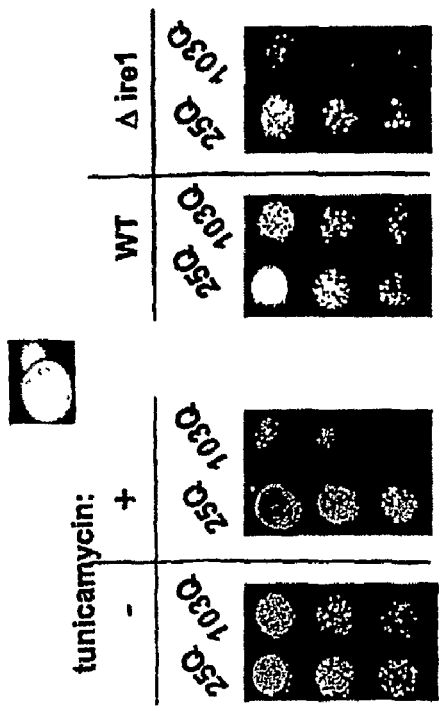
Figure 6E:
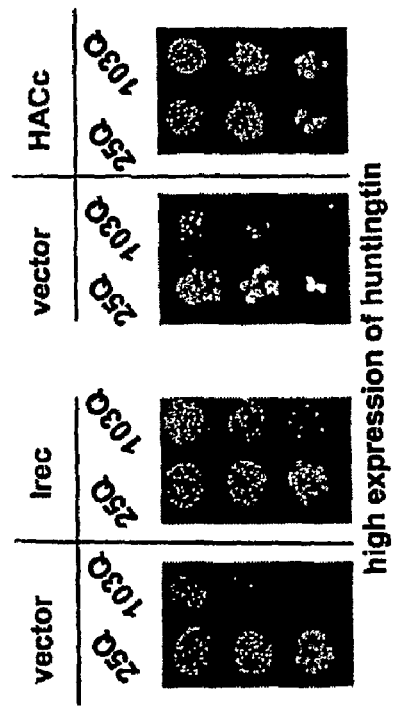
Figure 6A:
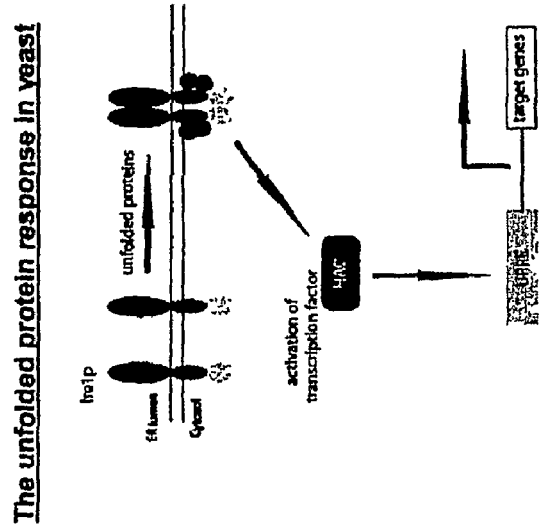

Huntingtin Toxicity is Enhanced by a Dysfunctional UPR and ER Stress and Ameliorated by an Activated UPR The unfolded protein response in yeast is depicted in FIG. 6A. Yeast cells grown in the presence of tunicamycin (FIG. 6B), a strong inducer of ER stress, or yeast cells having a deletion of IRE1 (FIG. 6C), a kinase that induces the UPR, showed enhanced toxicity when low levels of huntingtin were expressed in the yeast. Conversely, expression of constitutively active IRE1 or HAC (proteins that induce the UPR) ameliorated the toxic effects of high level expression of 103 Q huntingtin in yeast (FIGS. 6D and 6E).

Other Embodiments

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. A method of suppressing or reducing huntingtin-mediated toxicity in a neuronal cell, the method comprising inducing the expression or activity of a protein that induces the unfolded protein response (UPR) in the neuronal cell expressing huntingtin.

2. The method of claim 1, wherein the protein that induces the UPR is IRE1α or IRE1β.

3. The method of claim 1, wherein the protein that induces the UPR is IRE1α or IRE1β and the method comprises stimulating the activity of IRE1α or IRE1β by increasing one or more of dimer formation, phosphorylation, kinase activity, or RNase activity of the protein.

* * * * *